United States Patent [19]

Gregory

[11] 4,223,008

[45] Sep. 16, 1980

[54] SLOW RELEASE PHARMACEUTICAL COMPOSITIONS CONTAINING 3-[2-(4-BENZAMIDO-1-PIPERIDYL)ETHYL-]INDOLE, EMBONATE

[75] Inventor: George K. E. Gregory, Marlow, England

[73] Assignee: John Wyeth & Brother Limited, Maidenhead, England

[21] Appl. No.: 38,595

[22] Filed: May 14, 1979

[30] Foreign Application Priority Data

May 30, 1978 [GB] United Kingdom ............... 24646/78

[51] Int. Cl.² .......................... A61K 9/32; A61K 9/36
[52] U.S. Cl. ...................................... 424/32; 424/33; 424/35
[58] Field of Search ................................... 424/19–22, 424/32, 33, 35

[56] References Cited

U.S. PATENT DOCUMENTS

| | | | |
|---|---|---|---|
| 2,455,790 | 12/1948 | Malm et al. | 424/33 |
| 2,702,264 | 2/1955 | Klaui | 424/33 |
| 2,993,837 | 7/1961 | Millar et al. | 424/33 |
| 3,325,365 | 6/1967 | Hotko et al. | 424/33 |
| 3,775,537 | 11/1973 | Lehmann et al. | 424/21 |
| 3,835,221 | 9/1974 | Fulberth et al. | 424/20 |
| 3,954,959 | 5/1976 | Pedersen | 424/21 |
| 3,965,255 | 6/1976 | Bloch et al. | 424/19 |
| 4,001,390 | 1/1977 | Ohno et al. | 424/35 |
| 4,017,647 | 4/1977 | Ohno et al. | 424/33 X |
| 4,083,949 | 4/1978 | Benedikt | 424/19 |

OTHER PUBLICATIONS

C.A. 85, #116476u (1976), 84, #54073d (1976), 82, #68425r (1975), 80, #10485c (1974), 77, #56747f (1972), 77, #822J (1972), 76, #81327f (1972).

Primary Examiner—Shep K. Rose
Attorney, Agent, or Firm—Arthur E. Wilfond

[57] ABSTRACT

The invention provides a pharmaceutical composition in tablet form having an enteric coating and comprising 3-[2-(4-benzamido-1-piperidyl)ethyl]indole, embonate and a pharmaceutically acceptable carrier useful as a prolonged release antihypertensive formulation.

3 Claims, No Drawings

SLOW RELEASE PHARMACEUTICAL COMPOSITIONS CONTAINING 3-[2-(4-BENZAMIDO-1-PIPERIDYL)ETHYL]INDOLE, EMBONATE

This invention relates to slow release pharmaceutical compositions containing an indole derivative.

In UK Patent Specification No. 1,218,570 there are described and claimed a class of indole derivatives which have various pharmacological activities, especially action on the cardiovascular system. One of these compounds 3-[2-(4-benzamido-1-piperidyl)ethyl]indole has demonstrated valuable antihypertensive properties in human beings as shown in clinical trials. This compound, which has the international approved name, indoramin, is generally used in the form of its hydrochloride salt.

A novel salt, namely the embonic acid salt, has shown potent antihypertensive activity in a standard test. This salt is described and claimed in co-pending U.S. pat. application Ser. No. 38,596 filed the same day. present application in the name of John Leheup Archibald.

I have now surprisingly found from standard dissolution tests that the embonate salt of indoramin is particularly useful when employed in formulations where it is desired to achieve slow release of indoramin.

In the standard test, the embonate salt of indoramin was found to have an intrinsic dissolution rate different from the hydrochloride salt in solutions at medium pH. However, dissolution rates of embonate and hydrochloride at low pH were roughly equal. The procedure used in testing intrinsic dissolution rate was as follows:

Compress 250–500mg raw drug into a smooth cylindrical pellet in a 1.3cm diameter punch and die set, using a suitable laboratory pressure (apply 1–2 tons pressure and attach die to vacuum pump for 10 minutes, compress at 10 tons pressure). Eject the pellet from the die and check that it is free from superficial cracks.

Mount pellet centrally on a one inch square section of a microscope slide. Fix with paraffin wax so that the entire upper pellet face is exposed and place centrally at bottom of dissolution flask.

At zero time, pour 200ml dissolution medium (0.06NHCl or distilled water, at 37° C.±0.5° C.) into the flask. Check that pellet is undisturbed, start stirrer and timer.

Withdraw 10 ml samples of medium every 10 minutes over an hour through a sintered glass filter. Replace the same volume of dissolution medium at 37° C.±0.5° C. after each sampling, to maintain constant volume.

Filter each sample through a pre-washed 1.2μ millipore filter in Swinnex holder immediately prior to assay. Assay samples by uv absorbance measurement at 280nm in 1cm quartz cells. Compare with standard solutions (5–30μgml$^{-1}$) and calculate mg indoramin released from each sampling time by reference to the standard graph (concentration plotted against absorbance).

Results of testing are shown below:

| Intrinsic Dissolution Rates in mg per minute per sq cm | | |
|---|---|---|
| | Dissolution Medium | |
| Indoramin Salt Tested | 0.06 NHCl (pH 1.2) | Distilled Water |
| Embonate | 0.062 | 0.005 |
| Hydrochloride | 0.062 | 0.424 |

| Intrinsic Dissolution Rates in mg per minute per sq cm | | |
|---|---|---|
| | Dissolution Medium | |
| Indoramin Salt Tested | 0.06 NHCl (pH 1.2) | Distilled Water |
| | 0.062 | 0.409 |

The results show that the embonate salt and the hydrochloride salt of indoramin have similar dissolution rates at low pH such as found in the stomach. However, at higher pH such as found in the small intestine the rate of dissolution for the embonate salt is much slower than for the hydrochloride and also slower than the value for low pH.

Therefore the embonate salt of indoramin can be employed as a means for prolonging the release of indoramin when administered as en enteric coated tablet designed to release the embonate in the small intestine. Such prolonged release dosage forms are preferred in antihypertensive therapy where patients require treatment for a considerable length of time. This is because administration of the drug need not be as frequent as with ordinary release forms and can be reduced, for example, to once a day. As a result patient compliance with long term therapy is generally improved.

Accordingly, this invention provides a pharmaceutical composition in tablet form comprising the embonic addition salt of indoramin together with a pharmaceutically acceptable carrier, said tablet having an enteric coating. The carrier may be any suitable solid carrier known in the art.

The enteric coating may be any suitable coating known in the art. Examples of film forming substances for use in the enteric coating are hydroxypropylmethyl cellulose phthalate, polyvinyl acetate phthalate and acrylic resin. Plasticizers and lubricants may also be present. The coating may be sprayed onto the tablet core using a suitable solvent carrier. Typically the enteric coating comprises about 3 to about 5% of the tablet weight.

The particular dosage will depend on standard pharmaceutical practice. Typical doses for the enteric coated tablet are 200–800 mg indoramin per day, preferably 300–500 mg per day.

The following Example 1 illustrates the preparation of indoramin embonate. Example 2 illustrates the invention.

EXAMPLE 1

3-[2-(4-Benzamido-1-piperidyl)ethyl-indole, embonate

A suspension of 3-[2-(2-(4-benzamido-1-piperidyl)ethyl]-indole (3.47g, 0.01m) and embonic acid (1.94g, 0.05m) is refluxed in 200 mls of absolute ethanol until the solid dissolves. The hot solution is filtered and the solvent evaporated to give a gum. Water is added and the gum scratched until crystallisation occurs (5.4g) m.p. 175°–177° C.

Found: C, 74.08%; H, 6.24%; N, 7.55% $(C_{22}H_{25}N_3O)_2 \cdot C_{23}H_{10}O_6$ requires C, 74.29%; H, 6.14%; N, 7.76%.

EXAMPLE 2

Enteric Coated Indoramin Embonate Tablets

Cores for enteric coated tablets are made to the following two formulations:

|  | 1 | 2 |
|---|---|---|
| Indoramin Embonate | 77.95 (50) | 155.89 (100) |
| Amberlite IRP 88 | 7.0 | 14.0 |
| Avicel pH 101 | 108.0 | 229.23 |
| Lactose BP | 156.18 | — |
| Magnesium Sterile BP | 0.875 | 0.875 |
|  | 350.0 mg | 400.0 mg |

The figures in parentheses represent the weight of indoramin free base per tablet.

The process used is described briefly below:
1. Screen indoramin embonate, Avicel, Lactose 40 mesh—mix in suitable mixer.
2. Wet granulate with water to produce dense mass.
3. Wet screen 12–14 mesh.
4. Dry granulate-screen 16–20 mesh.
5. Compress.

Cores made according to the above are then sprayed with a solution of one of the following enteric coatings:

| Coating Composition | | |
|---|---|---|
| (a) | Hydroxypropylmethyl cellulose phthalate | 85% |
|  | Acetylated monoglyceride (Myvacet) | 10% |
|  | Talc | 5% |
| (b) | Eudragit L30D | 90% |
|  | Triacetin | 3.3% |
|  | Talc | 6.7% |
| (c) | Polyvinyl acetate phthalate | 95% |
|  | Stearic acid | 5% |

Water is a suitable solvent for coatings (a) and (b). For coating (c) a suitable solvent is a mixture of industrial methylated spirit/111-trichloroethane. The enteric coating forms 3–5% of the tablet weight.

I claim:
1. A pharmaceutical composition in tablet form having an enteric coating and comprising 3-[2-(4-benzamido-1-piperidyl)ethyl]indole, embonate in association with a pharmaceutically acceptable carrier.
2. A pharmaceutical composition as claimed in claim 1 wherein the enteric coating comprises about 3–5% by weight of the tablet.
3. A pharmaceutical composition as claimed in claim 1 wherein the enteric coating comprises a film forming substance selected from hydroxypropylmethyl cellulose phthalate, polyvinyl acetate phthalate and acrylic resin.

* * * * *